United States Patent [19]
Donskoy

[11] Patent Number: 5,895,364
[45] Date of Patent: Apr. 20, 1999

[54] NON-INVASIVE TECHNIQUE FOR BONE MASS MEASUREMENT

[75] Inventor: Dimitri Donskoy, Hoboken, N.J.

[73] Assignee: The Trustees of Stevens Institute of Technology, Hoboken, N.J.

[21] Appl. No.: 08/973,315

[22] PCT Filed: Jun. 20, 1996

[86] PCT No.: PCT/US96/10738

§ 371 Date: Nov. 25, 1997

§ 102(e) Date: Nov. 25, 1997

[87] PCT Pub. No.: WO97/00643

PCT Pub. Date: Jan. 9, 1997

[51] Int. Cl.$^6$ ........................................... A61B 5/03
[52] U.S. Cl. ........................................... 600/595
[58] Field of Search ........................... 600/587, 595; 33/511, 512, 515

[56] References Cited

U.S. PATENT DOCUMENTS

| | | | |
|---|---|---|---|
| 4,926,870 | 5/1990 | Brandenburger | 128/660.01 |
| 5,273,028 | 12/1993 | McLeod et al. | 128/33 |
| 5,402,781 | 4/1995 | Dimarogonas | 128/653.1 |
| 5,493,788 | 2/1996 | Richardson | 332/512 |

OTHER PUBLICATIONS

Doherty et al., "Evaluation of the Use of Resonant Frequences to Characterize Physical Properties of Human Long Bones", *J. Biomechan.* 1974 7:559–561.

Faulkner et al., "Noninvasive Measurements of Bone Mass, Structure, and Strength: Current Methods and Experimental Techniques".*Am. J. Roentgenology* 1991 157:1229–1237.

Grampp et al., "Current Methods and Perspectives", *The Radiological Clinics of North America* 1993 31(5):1133–1141.

Jurist, J.,"In $^{Vivo}$ Determination of the Elastic Response of Bone I. Method of Ulnar Resonant Frequency Determination".*Phys. Med. Biol.* 1970 15:417–426.

Orne, D., "The $^{In\ Vivo}$ Driving–Point Impedance of the Human Ulna–A Viscoelastic Beam Model", *Biomechanics* 1974 7:249–257.

Praemer et al., "Musculoskeletal Conditions in the United States".*American Academy of Orthopaedic Surgeons* 1992 46–52.

Saha, S. and Lakes, R.S., "The Effect of Soft Tissue On Wave–Propagation and Vibration Tests For Determining The $^{In\ Vivo}$ Properties of Bone".*J. Biomechan.* 1977 10:393–401.

Selle, W.A. and Jurist, J.M., "The Onset of Postmenopausal Osteoporosis as Studied By a New Technique", *J. Am. Geriat. Soc.* 1966b 14: 930.

Thompson et al., "In $^{Vivo}$ determination of mechanical properties of the human ulna by means of mechanical impedance tests: Experimental results and improved mathematical model", *Med. Biol. Eng.* 1976 14: 253–262.

Wand et al., "The Relationship Between Ultrasound and Densitometric Measurements of Bone Mass at the Calcaneus in Women", *Calcif. Tissue Int.* 1992 51: 415–418.

*Primary Examiner*—Max Hindenburg
*Attorney, Agent, or Firm*—Law Offices of Jane Massey Licata

[57] ABSTRACT

The present invention provides an apparatus for noninvasive determination of bone mass, said apparatus having a platform for supporting a bone to be measured, a spring having a selected stiffness which connects the platform to a sensor capable of measuring vibration velocity and force, and a vibrating means connected to the sensor, wherein the vibrating means exposes the sensor, the spring and the platform to vibration so that vibration velocity and force can be measured by the sensor and the mass of the bone determined. A second apparatus for noninvasive determination of bone mass having a gripping means, a spring having a selected stiffness which connects the gripping means to a platform for positioning of a bone, a sensor capable of measuring vibration velocity and force which connects the platform to a vibrating means, and a vibrating means which vibrates the sensor, the platform, the spring, and the gripping means so the vibration velocity and force can be measured by the sensor is also provided. In addition, a method of noninvasively determining mass of a bone with these apparatuses is provided.

4 Claims, 3 Drawing Sheets

NON-INVASIVE TECHNIQUE FOR BONE MASS MEASUREMENT

FIELD OF THE INVENTION

This invention relates generally to bone quality assessment, and, more particularly, relates to bone mass measurement and monitoring in a patient which can be used for the diagnosis of osteoporosis.

BACKGROUND OF THE INVENTION

Existing techniques for bone quality assessment are based on photon and X-ray absorptiometry and X-ray quantitative computed tomography. Gramp et al. *The Radiological Clinics of North America* 1993 31(5):1133–1141; Faulkner et al. *Am. J. Roentgenology* 1991 157:1229–1237. Each of these methods are routinely used in clinical practice. However, these techniques have limited applicability because of expensive and bulky equipment and potential risk of radiation during the procedure.

The application of acoustic energy for non-invasive skeletal diagnosis has also been shown to be feasible and has advantages for bone mass and strength measurement. Jurist, *J. Phys. Med. Biol.* 1970 15:417–426; Orne, D. *Biomechanics* 1974 7:249–257; Thomson et al. *Med. Biol. Eng.* 1976 14:253–262; Saha, S. and Lakes, R. S., *J. Biomechan.* 1977 10:393–401; Doherty et al. *J. Biomechan.* 1974 7:559–561; Waud et al. *Calcif. Tissue Int.* 1992 51:415–418; Selle, W. A. and Jurist, J. M. *J. Am. Geriat. Soc.* 1966b 14:930. Unlike conventional radiological techniques, acoustic techniques emit no radiation, are cost effective, and utilize equipment which is portable and easy to operate. Subsonic techniques for determining the in vivo properties of bone, known as impedance and resonance methods are based on measurement of the response of a bone to a flexural wave excitation in the frequency range 200 to 1000 Hz. A correlation between the resonance frequency of the human ulna and osteoporosis has been reported. However, while a significant number of acoustic tests have been performed, these techniques have not been used as a bone diagnostic tool for clinical application because of difficulties in the interpretation of the measurements. Ultrasound velocity and attenuation depend on density as well as on certain other properties of bone. A recent report showed that only 53% of broadband ultrasound attenuation (BUA) value and 44% of velocity of sound (VOS) value can be accounted for by bone density. Waud et al. *Calcif. Tissue Int.* 1992 51:415–418. Interpretation of subsonic measurement of flexural vibration of bone is also a difficult task and to a great extent, depends upon a corresponding mathematical model of the test object. The effect of soft tissues creates additional difficulties in the interpretation and use of these techniques.

A non-invasive, nonhazardous and cost effective infrasound resonance method for the quantitative measurement and monitoring of bone quality has now been developed involving the measurement of the rigid body longitudinal resonance of a bone. Instrumentation for making these measurements is also provided.

SUMMARY OF THE INVENTION

An object of the present invention is to provide a noninvasive apparatus for measuring force and vibration velocity to determine the mass of a bone which comprises a platform for supporting a bone to be measured, a spring having a selected stiffness which connects the platform to a sensor capable of measuring vibration velocity and force, and a vibrating means connected to the sensor, wherein the vibrating means exposes the sensor, the spring and the platform to vibration so that vibration velocity and force can be measured by the sensor and the mass of the bone determined.

Another object of the present invention is to provide a method of noninvasively measuring vibration velocity and force to determine the mass of a bone which comprises positioning a bone to be measured on a platform wherein the platform is attached to a spring having a selected stiffness, exposing the platform to vibration wherein the vibration is generated by a vibrating means, and measuring vibration velocity and force to determine bone mass.

DETAILED DESCRIPTION OF THE INVENTION

Figure 1:
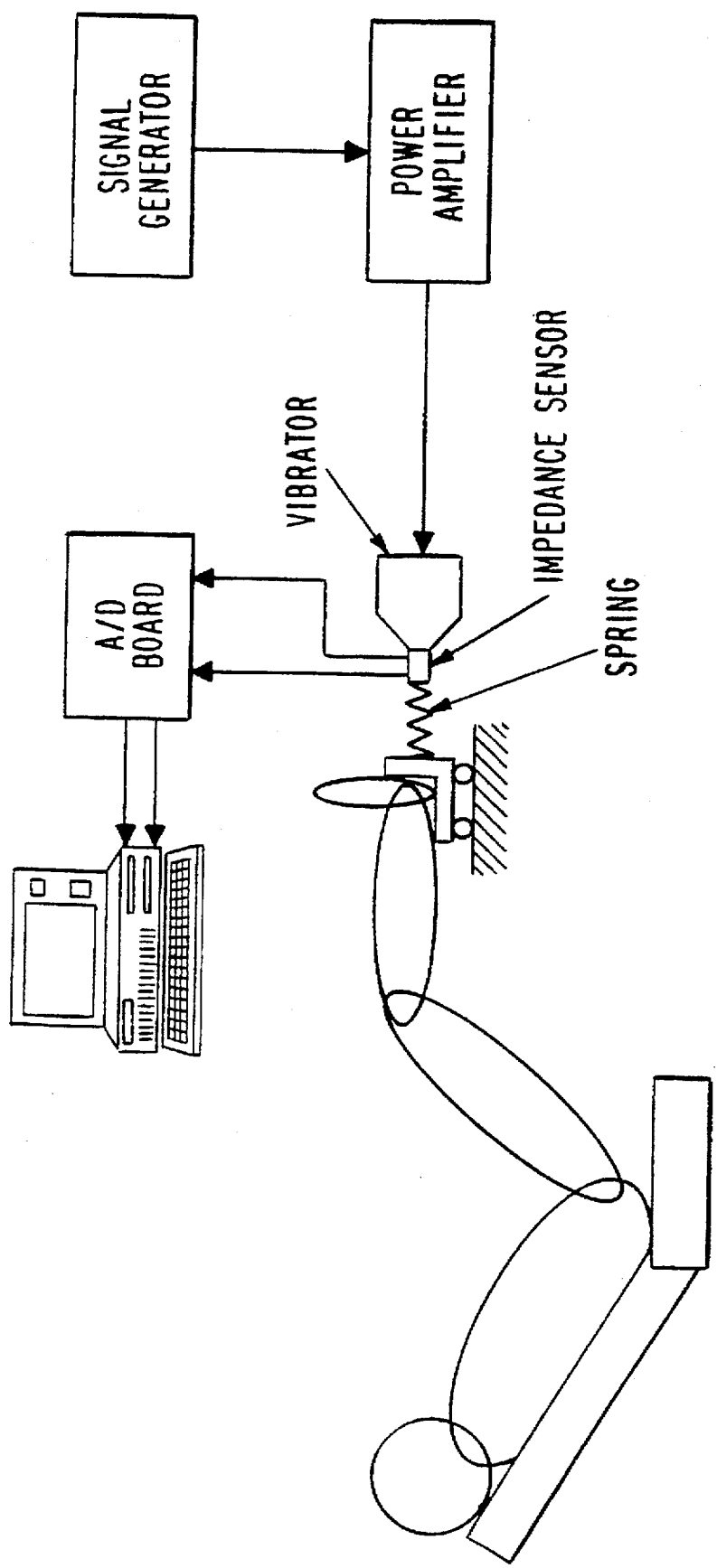
FIG. 1 provides a block diagram of a subsonic mechanism for quantitative measurement of bone quality.

With the increasing age of the population, there is a great interest in the diagnosis, treatment and health care costs relating to osteoporosis. Available data indicates that 56.7% of women 45 years of age and older have osteoporosis. Praemer et al. *American Academy of Orthopaedic Surgeons* 1992 46–52. Current methods for monitoring bone quality and diagnosing osteoporosis have limited applicability because of expensive and bulky equipment and procedures and the potential risk of radiation.

A cost effective subsonic technique and compact, low cost instruments have now been developed for the quantitative measurement of bone quality and the diagnosis of osteoporosis. This technique can be used by general practitioners, physicians and rehabilitation specialist, requiring no specific training and expertise for use. In the present invention, the rigid body longitudinal resonance of a bone, preferably the tibia or ulna, is measured with the use of an artificial spring having a known stiffness. This procedure simplifies the interpretation of the measurements and is much more accurate than existing acoustic methods which measure flexural resonances involving both the mass and flexibility of a bone and the surrounding soft tissue.

In contrast to more conventional approaches which measure the response of a bone to flexural mode excitation, the present invention measures the response of a bone to longitudinal excitation through an artificial spring. With this method, the mechanical model of the body is greatly simplified by selection of an appropriate artificial spring.

In one embodiment, bone mass is determined by measuring vibration velocity and force with an apparatus which comprises a platform for supporting a bone to be measured, a spring having a selected stiffness which connects the platform to a sensor capable of measuring vibration velocity and force, and a vibrating means connected to the sensor, wherein the vibrating means exposes the sensor, the spring and the platform to vibration so that vibration velocity and force can be measured by the sensor. The ratio of the vibration force versus the velocity is the mechanical impedance which provides information concerning the mass of the bone. In a preferred embodiment, the apparatus further comprises an FTT analyzer which converts the vibration velocity and force measured by the sensor into impedance. This impedance is very sensitive to a variation of bone mass and is not sensitive to soft tissue mass variation. Therefore, the mass of the bone can be measured independently of variations in bone flexibility and soft tissue parameters.

In another embodiment, bone mass is measured with an apparatus which comprises a gripping means, a spring having a selected stiffness which connects the gripping means to a platform for positioning of a bone, a sensor capable of measuring vibration velocity and force which connects the platform to a vibrating means, and a vibrating means which vibrates the sensor, the platform, the spring, and the gripping means so the vibration velocity and force can be measured by the sensor. The ratio of the vibration force versus velocity is the mechanical impedance which provides information concerning the mass of the bone.

Figure 2A:
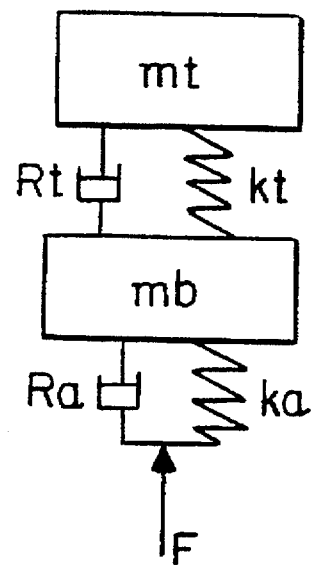
FIGS. 2a and 2b provide equivalent mechanical (FIG. 2a) and electrical (FIG. 2b) diagrams of the driver-spring-tibia/ulna system. F is an external vibromotive force, ka and Ra are stiffness and damping coefficients of the artificial spring, respectively, Kt and Rt are stiffness and damping coefficients of the overlying soft tissue and mb is the mass of the bone and the fixing platform.
Figure 2B:
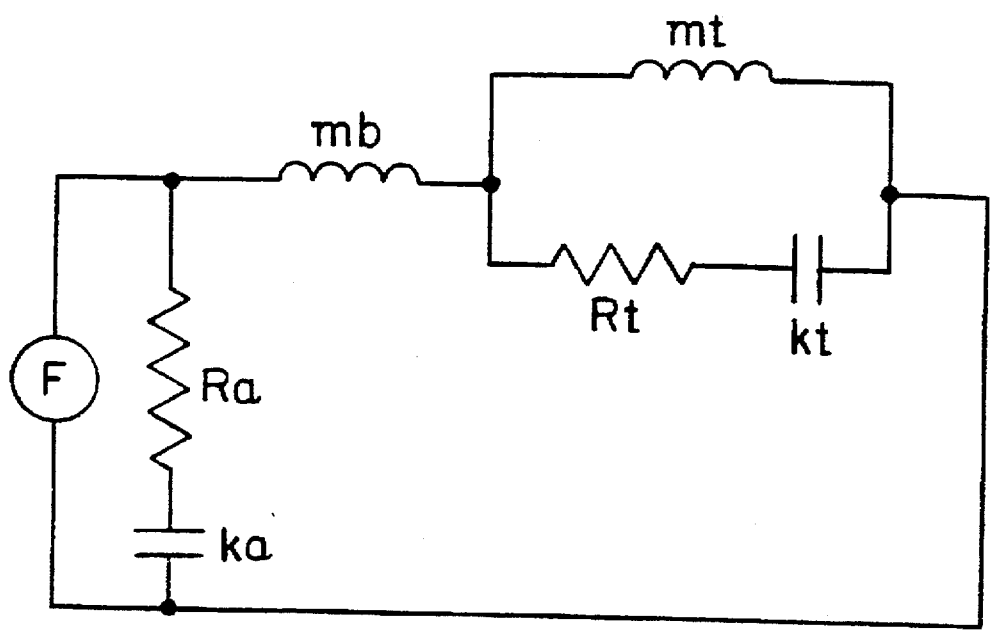
Figure 3:
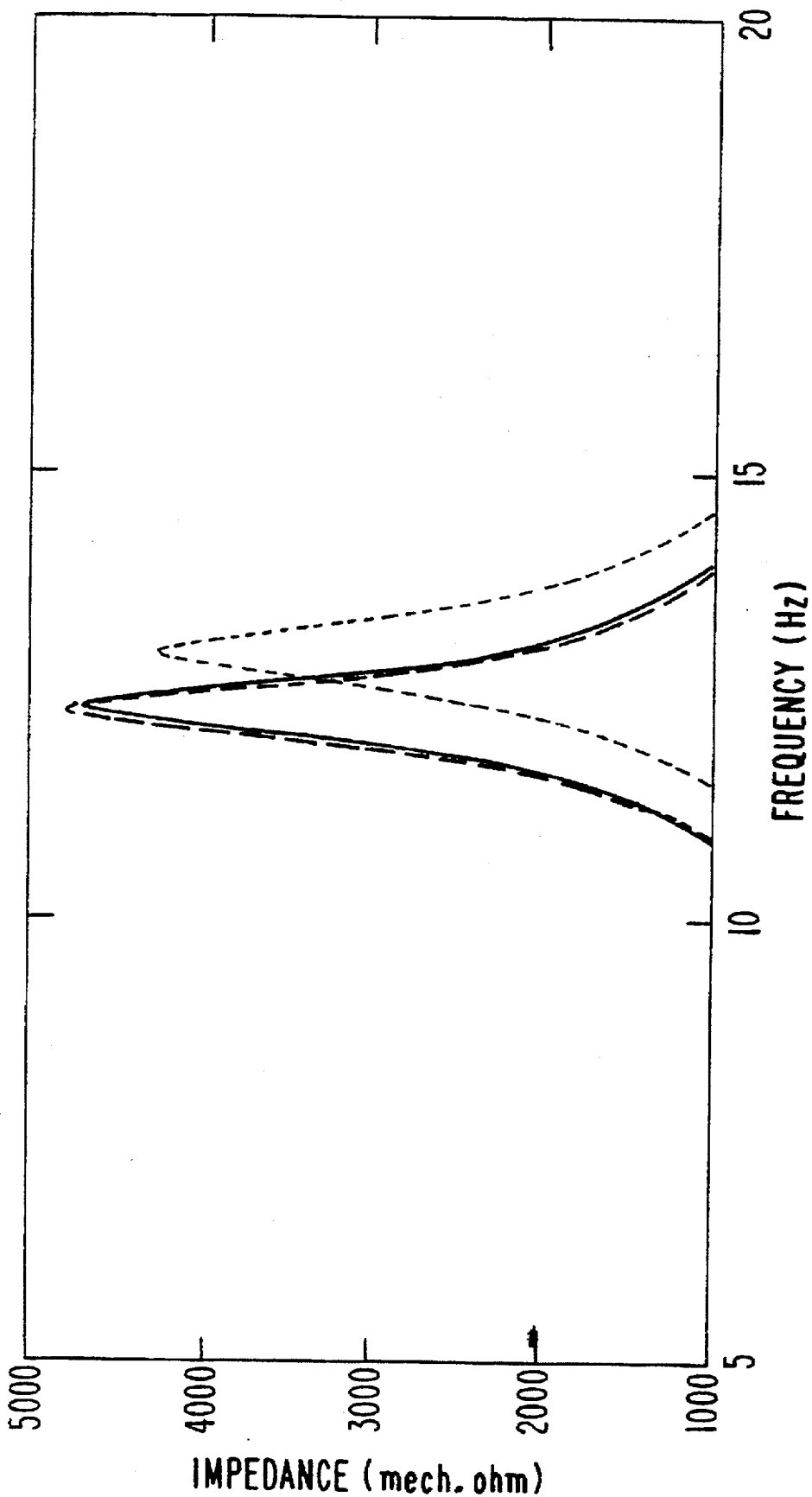
FIG. 3 represent the results of calculations of the driving point impedance vs. driving frequency. The dashed curve corresponds with 80% variation of soft tissue mass. The dotted curve corresponds with 10% variation of bone mass. This figure shows that the deviation of resonance peak is sensitive to mass of bone variation and is not susceptible to overlying soft tissue.

For the purposes of the present invention, by a "spring having a selected stiffness" it meant that the spring may have stiffness $k_a$ much less than the stiffness of the bone $k_b$ and the joints $k_j$, but stiffer than the stiffness of soft tissues $k_t$, i.e. $k_t \ll k_a \ll k_b, k_j$. According to Orne (Biomechanics 1974 7:249–257), $k_t = 10^3 + 10^4$ dyn/cm, $k_b$, $k_j = 10^8 + 10^{10}$ dyn/cm. Therefore, if the stiffness of the artificial spring, $k_a$, is in the range of $10^5 + 10^7$ dyn/cm, the flexibility of the bone and joints are negligible and the mechanical and equivalent electrical model of a bone in the correspondent frequency range can be represented as shown in FIG. 2, wherein F is an external vibromotive force, $k_a$ and $R_a$ are stiffness and damping coefficients of the artificial spring, respectively, $k_t$ and $R_t$ are stiffness and damping coefficients of the soft tissue and mb is the mass of the bone and a fixing platform. This system has a resonance. In the vicinity of the resonance the driving point impedance is very sensitive to a variation of bone mass, does not depend on flexibility of bone, and is not sensitive to soft tissue mass and damping effect.

Using this apparatus bone mass is measured noninvasively by positioning a bone to be measured on the platform for support wherein the platform is attached to a spring having a selected stiffness. The platform and spring are then exposed to vibration resulting from the vibration means and vibration velocity and force are measured by an impedance sensor attached to the spring. Based upon the ratio of vibration force versus velocity, a mechanical impedance is calculated and mass of the bone is determined. This determination is independent of variations in bone flexibility and soft tissue parameters.

The present invention provides a light weight, compact and relatively inexpensive instrument which can be used for quantitative measurements as well as monitoring of bone mass and bone quality. The present invention is especially useful in the diagnosis and detection of osteoporosis. In addition, the present invention offers a non-hazardous method as compared with general X-ray techniques for general practitioners, physicians and rehabilitation specialist to monitor bone quality with the requirement for radiation certification.

What is claimed is:

1. A noninvasive apparatus for determining mass of a bone comprising:

(a) a platform for supporting a bone;

(b) a sensor capable of measuring vibration velocity and force;

(c) a spring having a selected stiffness which connects the platform to the sensor; and (d) a vibrating means connected to the sensor, wherein the vibrating means exposes the sensor, the spring and the platform to vibration so that vibration velocity and force can be measured by the sensor and mass of the bone supported by the platform determined.

2. The apparatus of claim 1 further comprising an FTT analyzer which converts the vibration velocity and force measured by the sensor into impedance.

3. A noninvasive apparatus for determining mass of a bone comprising:

(a) a gripping means;

(b) a platform for supporting a bone;

(c) a spring having a selected stiffness which connects the gripping means to the platform;

(c) a sensor capable of measuring vibration velocity and force which connects the platform to a vibrating means; and (d) a vibrating means which vibrates the sensor, the platform, the spring, and the gripping means so that the vibration velocity and force can be measured by the sensor and mass of the bone suported by the platform determined.

4. A method of noninvasively determining mass of a bone comprising:

(a) positioning a bone to be measured on a platform, wherein the platform is attached to a spring having a selected stiffness;

(b) exposing the platform to vibration, wherein the vibration is generated by a vibrating means; and (c) measuring vibration velocity and force to determine mass of the bone.

* * * * *